United States Patent [19]

Mower et al.

[11] Patent Number: 5,346,506
[45] Date of Patent: Sep. 13, 1994

[54] METHOD FOR ESTABLISHING DEFIBRILLATION THRESHOLD FOR A CARDIAC DEFIBRILLATOR

[76] Inventors: Morton M. Mower, 5501 Village Dr., #302, Edina, Minn. 55435; Peng S. Chen, 474 Paulette Pl., La Canada, Calif. 91011

[21] Appl. No.: 974,049

[22] Filed: Nov. 10, 1992

[51] Int. Cl.$^5$ .............................................. A61N 1/39
[52] U.S. Cl. ...................................................... 607/7
[58] Field of Search .............................. 607/5, 6, 7, 8

[56] References Cited

U.S. PATENT DOCUMENTS 5,105,809 4/1992 Bach, Jr. et al. ........................ 607/7

*Primary Examiner*—William E. Kamm
*Assistant Examiner*—Scott M. Getzow
*Attorney, Agent, or Firm*—Keck, Mahin & Cate

[57] ABSTRACT

A method of determining a defibrillation threshold for an implantable cardiac defibrillator, based upon determining the 50% probability of reaching the upper limit of vulnerability. The 50% probability of reaching the upper limit of vulnerability at the mid-upslope of the T-wave is found to closely approximate the 50% probability of successful defibrillation used to set the shock energy level of the defibrillator. A delayed up-down algorithm is used to determine the shock strength associated with 50% probability of reaching the upper limit of vulnerability.

1 Claim, 3 Drawing Sheets

METHOD FOR ESTABLISHING DEFIBRILLATION THRESHOLD FOR A CARDIAC DEFIBRILLATOR

FIELD OF THE INVENTION

The present invention is related to the art of cardiac defibrillation, and in particular, is concerned with an improved method of determining the minimum energy required to defibrillate the heart of a patient. In accordance with the improved method, the number of ventricular fibrillation episodes required for the determination is reduced, as is the total energy of the pulses applied to the heart.

BACKGROUND OF THE INVENTION

In the field of cardiac defibrillation, it is well known that the energy required to effectively defibrillate a human heart, varies with internal lead configuration and electrode placement, as well as with the responsiveness of a particular patient's heart. It is necessary to determine, with the highest degree of accuracy, the minimal energy level necessary to defibrillate a patient's heart using implanted defibrillation leads.(the defibrillation threshold).

One known method of determining the defibrillation threshold energy of an implantable system is to induce fibrillation of a patient's heart. Once fibrillation occurs, the heart is defibrillated through the implanted defibrillation leads. Initially, defibrillation is attempted at a relatively high energy level (high energy being used to ensure rapid defibrillation and hence minimize patient risk). If this energy level defibrillates the heart, the heart is placed in fibrillation again, and a defibrillation pulse of a lower energy level is applied to the heart. If the lower energy level defibrillates the heart, the process is repeated with even lower defibrillation pulse energy levels until the heart is not defibrillated. The defibrillation energy level for the permanently implanted device is then set, according to the physician's discretion, above that energy level which reliably defibrillates the heart.

A disadvantage of the aforementioned method is the need to repeatedly induce fibrillation in a patient's heart, and to repeatedly defibrillate the heart to determine the system thresholds.

Another method of determining defibrillation thresholds is set forth in U.S. Pat. No. 5,105,809, issued on Apr. 21, 1992. The method described in this patent begins by applying an initial electrical shock to the heart during a period of vulnerability, usually occurring contemporaneously with the T-wave of a conventional ECG. The energy level of the initial shock is sufficient high so as not to cause fibrillation. Assuming the initial shock fails to induce fibrillation, a second electrical shock is applied during a subsequent period of vulnerability, the second shock having a magnitude less than the initial shock. Subsequent shocks are then applied, each with a magnitude smaller than the preceding shock, until fibrillation is induced. When fibrillation finally occurs, the energy of the preceding shock (the last to not cause fibrillation), is deemed to be the energy level required to defibrillate via that particular lead configuration.

However, because the period of vulnerability differs from patient to patient (thus is not precisely known), and is not necessarily contemporaneous with the appearance of a T-wave, for best results the aforementioned procedure must be performed several times, each time corresponding to a different possible time interval of vulnerability. That is, the procedure is performed numerous times over distinct time intervals to insure that the shocks used to determine the defibrillation threshold were applied during a true period of vulnerability. This results in the patient being subjected to numerous shocks and several fibrillation episodes (though fewer than prior techniques) in an attempt to determine the defibrillation threshold.

SUMMARY OF THE INVENTION

It is a primary object of the present invention to further reduce the number of fibrillation episodes and the amount of energy applied to determine the minimal defibrillation energy of an implantable defibrillation system.

It is another object of the present invention to provide a method of determining a defibrillation threshold whereby both the number of fibrillation episodes and the amount of energy applied is minimized, while still maintaining the desired accuracy of the threshold determination.

The present invention provides an improved method of determining the defibrillation threshold for an individual patient provided with a particular electrode and lead configuration.

Research has demonstrated that the 50% probability of successful defibrillation can be closely approximated by determining the 50% probability of reaching the upper limit of vulnerability. Thus, accurate determination of 50% probability of reaching the upper limit of vulnerability with a minimum number of fibrillation episodes, and with a minimum application of energy to the heart, will provide the desired value of the 50% probability of successful defibrillation. In accordance with this invention, the shock strength associated with the 50% probability of successful defibrillation is established by determining the 50% probability of reaching the upper limit of vulnerability. The 50% probability of reaching the upper limit of vulnerability is determined by a method in accordance with the invention which requires a reduced number of fibrillation episodes and the application of less total energy in each pulse. In particular, electrical energy is applied over a limited time interval during the period in which greatest vulnerability is most likely to occur. That is, the electrical energy is applied for a predetermined limited period of time following ventricular depolarization (the QRS complex), with this limited time period centered on the mid-upslope of the T-wave (repolarization period). By not having to scan the entire T-wave with shocks, the number of shocks is considerably reduced as compared to prior methods.

The energy level chosen for the first application is that estimated beforehand to be the 50% probability of reaching the upper limit of vulnerability. Further shocks are delivered based upon a delayed four-episode up-down algorithm. Such an algorithm is set forth in an article entitled: *An Up-Down Algorithm for Estimation of the Cardiac Ventricular Defibrillation Threshold*, by Wayne C. McDaniel and John C. Schuder in *Medical Instrumentation*, Volume 22, No. 6, December 1988, pages 286–292 beginning on page 288. In accordance with this procedure, the number of shocks required to determine the 50% probability of reaching the upper limit of vulnerability and accordingly the 50% probability of successful defibrillation is greatly reduced, particularly if the estimated 50% probability of reaching the upper limit of vulnerability is quite accurate.

The aforementioned and other objects, features, and advantages of the present invention will become subsequently apparent from the following description of the preferred embodiment, as well as from the associated drawings, all of which merely illustrate the inventive concept, and are in no way intended, nor should they be construed, to limit the scope of the instant invention.

DETAILED DESCRIPTION OF A PREFERRED EMBODIMENT

Figure 1:
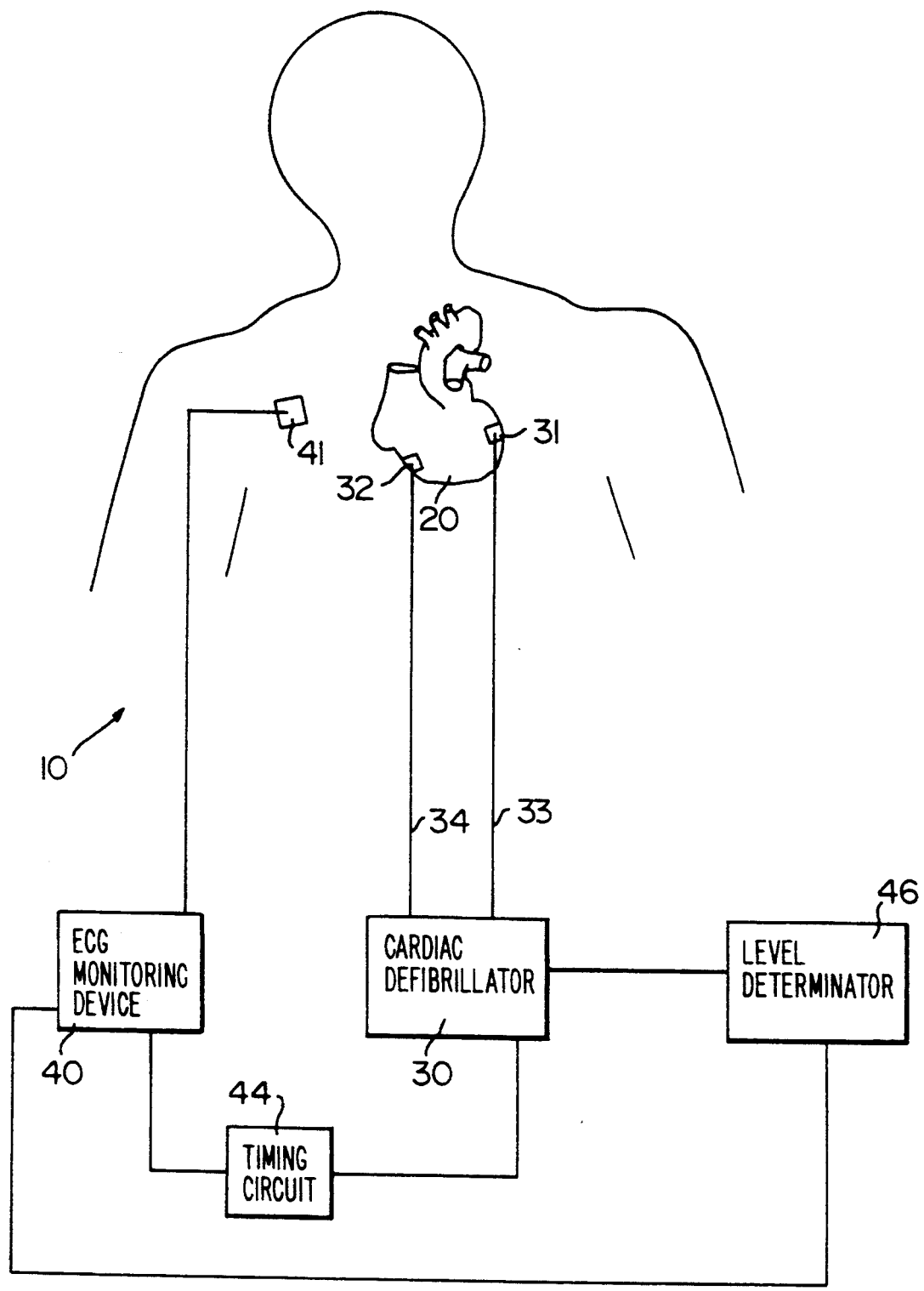
FIG. 1 illustrates a suitable defibrillator arrangement and system for determining a defibrillation threshold, in accordance with the present invention.

With reference to FIG. 1, an implantable defibrillation system 10 is shown comprising a defibrillator 30 having two leads 33 and 34 connected to two electrodes 31 and 32, respectively. The defibrillator 30, as well as the electrodes 31 and 32 and leads 33 and 34 can be of any design known to the art, and do not necessarily have to assume the configuration illustrated. Furthermore, an ECG monitoring device 40 and a timing circuit 44 are also included for providing the defibrillator 30 with a timing reference. As is the case for the defibrillator 30, the ECG monitoring device 40 and timing circuit 44 can be of any commonly known type. In accordance with this invention, the timing circuit 44, establishes the mid-upslope part of the T-wave and provides an appropriate signal indicative thereof to the cardiac defibrillation 30. Also, a level determinator circuit 46 is provided for controlling and monitoring the level of shocks generated by the defibrillator 30. The level determinator 46 may be a microprocessor based device and is connected to the ECG monitoring device 40 to disable the defibrillator 30 when appropriate, i.e. when fibrillation or defibrillation, as appropriate is successful.

Figure 2:
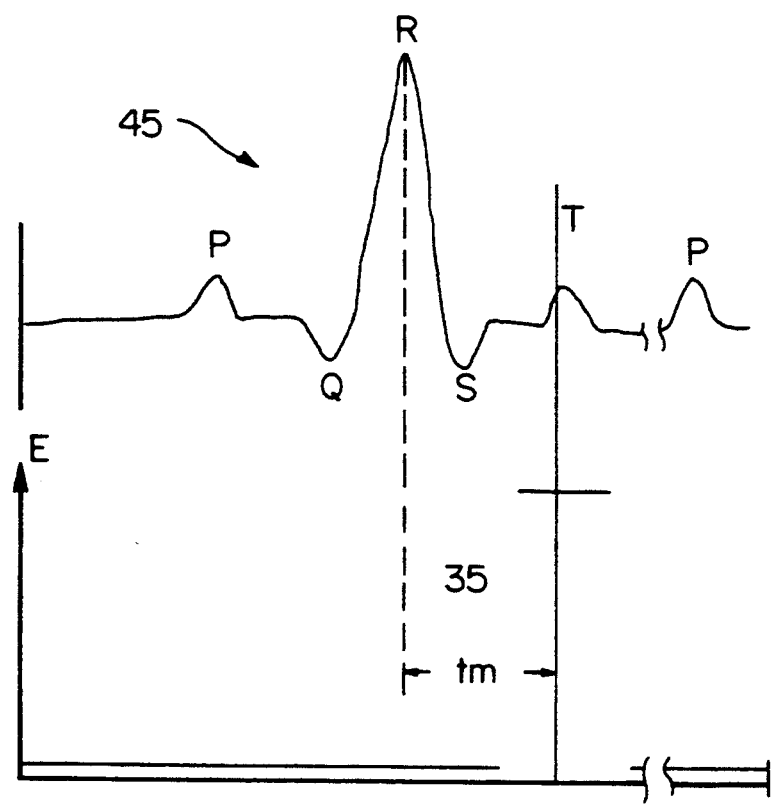
FIG. 2 is a timing diagram illustrating the relationship between cardiac timing and electrical shocks, in accordance with the present invention.
Figure 2A:
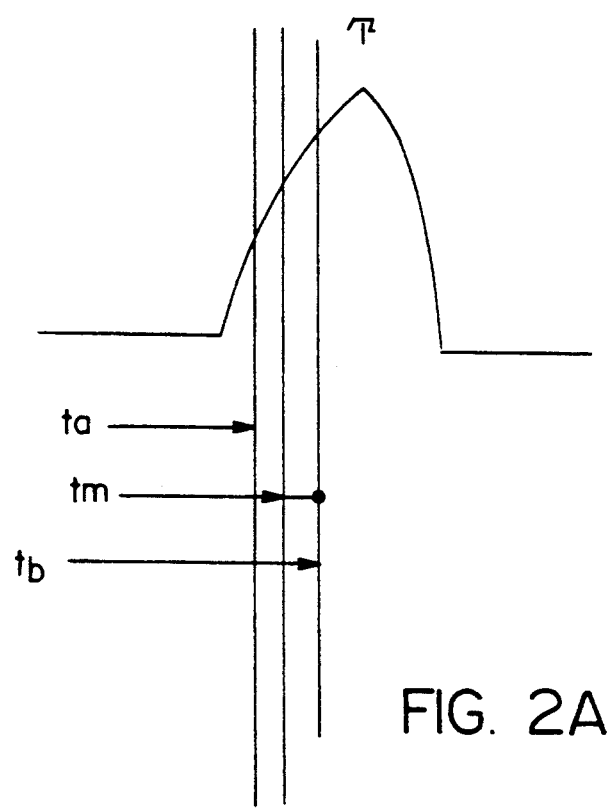
FIG. 2A is an enlarged portion of the timing diagram of FIG. 2 showing the T-wave.

FIG. 2 illustrates a typical waveform 45 produced by the ECG monitoring device 40 in response to the electrical activity of a human heart. In particular, the illustrated waveform 45 is a normal sinus rhythm waveform 45 produced by a normally functioning human heart 20. This sinus rhythm waveform 45 provides the basic timing reference to which the herein disclosed method is related. More particularly, the timing circuit establishes a reference $t_m$ for the mid-upslope part of the T-wave to the QRS complex as shown in FIG. 2A.

Since defibrillation thresholds vary with electrode placement and lead configuration, as well as with the responsiveness of a particular patient's heart, the defibrillation threshold is best determined after the electrodes and leads have been implanted. In this manner, the threshold corresponds to the particular arrangement used.

To more accurately determine the timing of the mid-upslope of the T-wave, the patient's heart is controlled by baseline pacing. That is, if a patient's intrinsic heart rate is 100 beats per minute, i.e. every 600 milliseconds, baseline pacing would be provided at 500 milliseconds to overdrive the natural heart rate. Then, if the shock is applied at approximately 300 milliseconds, it should be very close to the mid-upslope point of the T-wave. In applying the shock, better results have been found where the shock errors toward the peak of the T-wave then toward the beginning of the up-slope. A typical duration of the shock pulse in accordance with this invention is approximately 6 milliseconds for monophasic shocks and 12 milliseconds for biphasic shocks. When the patient is controlled by baseline pacing, eight to ten pacing pulses are applied prior to applying the shock.

In attempting to determine the upper level of vulnerability, if the final shock is applied at an energy level of 15 Joules, for the majority of patients, the shock will be above the 50% probability level of inducing ventricular fibrillation. After the patient's heart has rested for a short period, such as one minute, eight to ten pacing pulses would again be applied prior to applying a 10 Joules shock. If it is found desirable to establish ventricular fibrillation, the shocks would continue to be reduced in equal steps until ventricular fibrillation occurs. However, if the intent is to implant a 15 Joules device, the shocks need not be reduced below 10 Joules, even if ventricular fibrillation is not induced at 10 Joules. If the device to be implanted is not used to apply the shocks that determine the upper limit of vulnerability, the shocks should have the same waveform as those developed by the device to be implanted.

Figure 3:
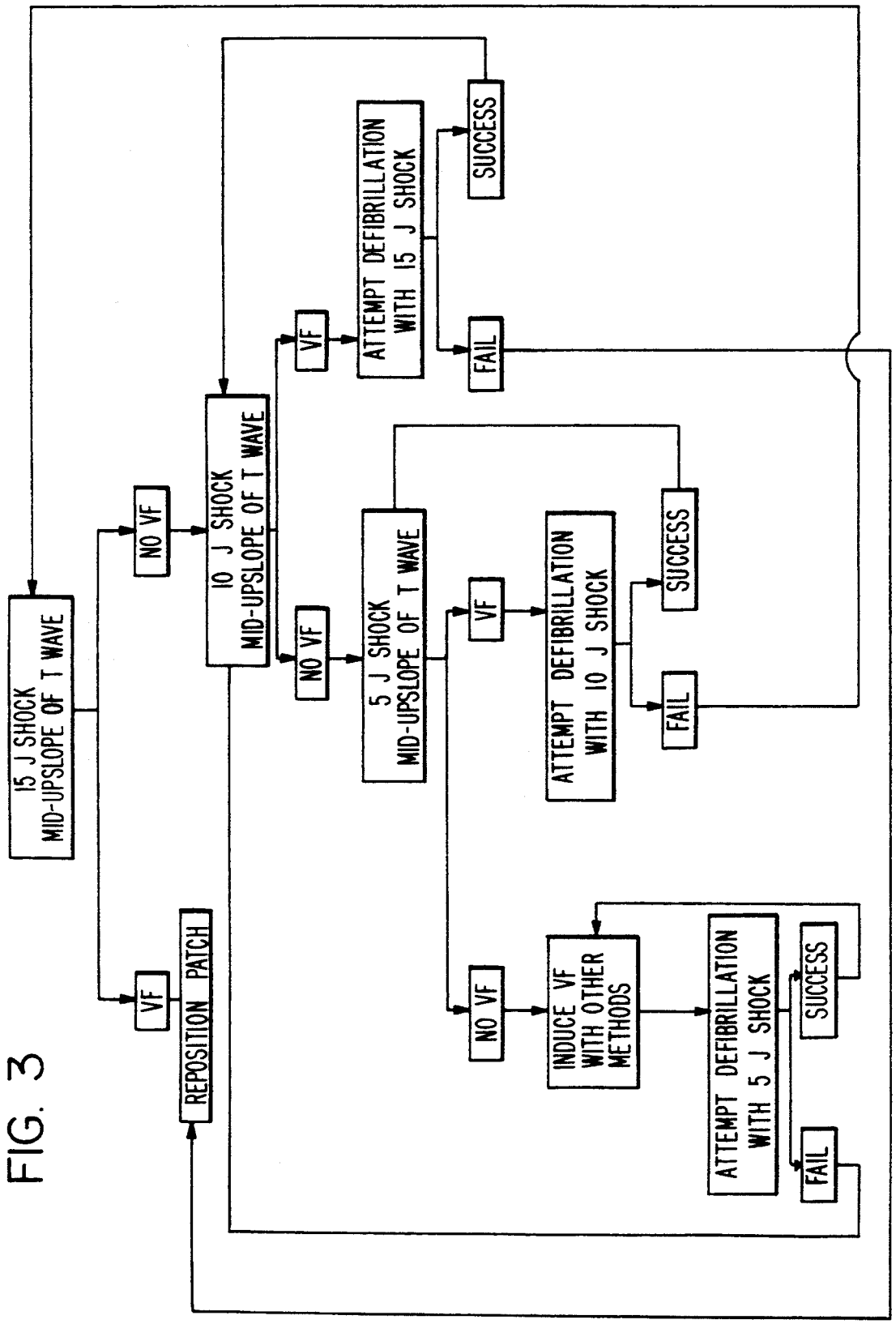
FIG. 3 is a block diagram depicting one possible sequence of steps in accordance with the method of the present invention.

Referring to FIGS. 1-3, the method according to the present invention will be described. The ECG signal is monitored for the occurrence of a QRS complex by the ECG monitoring device 40 through an appropriate sensing electrode 41. As soon as a QRS complex (ventricular depolarization) is detected, the defibrillator 30 is triggered by the timing circuit 44 to appropriately apply, at a predetermined time thereafter, an initial electrical shock 35. Specifically, the initial shock 35 is applied such that it centers on the mid-upslope of the T-wave, i.e., at time $T_m$ after the QRS complex. In a preferred embodiment of this invention the shock is a high voltage truncated exponential monophasic shock with 6 milliseconds pulse duration and variable tilt. Referring to FIG. 2A, the shock begins at $t_a$, 3 milliseconds before $t_m$ and ends at $t_b$, 3 milliseconds after $t_m$. The initial electrical shock 35 is set at an energy level which is the best a priori estimate of the 50% probability of reaching the upper limit of vulnerability. Subsequent shock are applied in accordance with a delayed four-episode, up-down algorithm, to determine the shock strength associated with a 50% probability of reaching the upper limit of vulnerability.

As an example of the method of this invention, starting just before the mid-upslope of the T-wave, time $t_a$ a test shock is applied with an estimated energy of 15 Joules. If the test shock failed to induce ventricular fibrillation, the energy of the next test shock would be reduced by a certain value $\delta$ which in one application of this invention was 5.0 Joules. The energy level of subsequent test shocks would continue to be reduced the same $\delta$ value, i.e., by 5 Joules until ventricular fibrillation is induced. The last test shock that did not induce ventricular fibrillation is used as the first data point for the "four-episode delayed up-down algorithm" used to determine the 50% probability of reaching the upper limit of vulnerability. The test shock that just induces ventricular fibrillation is taken as the second data point. The next test shock is then applied with an energy level 5.0 Joules higher than that establishing the second data point and is considered the third data point. If the test shock establishing the third data point is unsuccessful in establishing defibrillation, the energy of the next test shock is again increased by 5 Joules and is used as the fourth data point. The fifth data point can be predicted according to the results of the test shock establishing the fourth data point.

If the third test shock is successful in establishing defibrillation, the energy level of the next shock is reduced by 5 Joules and is taken as the fourth data point. Again, the fifth data point can be predicted according to the results of the fourth test shock. The average of the five data points is an accurate estimate of the 50% probability of reaching the upper limit of vulnerability which has been shown to also establish the 50% probability of successful defibrillation. Thus, by using this algorithm, the 50% probability of successful defibrillation can be determined with most patients undergoing only one or two episodes of ventricular fibrillation and receiving a limited number of shocks. It should be understood that any time defibrillation is not induced when desired by a test shock applied in accordance with the method of this invention, a salvage shock is immediately applied to defibrillation and restore the normal heart beat.

Based upon signals provided to the timing circuit by the ECG Monitor Device, QRS complexes are counted and used to establish suitable intervals between shocks to give the heart sufficient time to recover from the previously applied shock before any subsequent shocks are delivered.

Referring to FIG. 3 a diagram is provided of a protocol in accordance with that described above for determining the shock strength associated with 50% probability of successful defibrillation. Because of the close correlation between the upper limit of vulnerability and the defibrillation threshold, a shock that fails to induce ventricular fibrillation can be treated as a successful defibrillation shock and a shock that induces ventricular fibrillation can be treated as an unsuccessful defibrillation shock. In accordance with this diagram, the delayed up-down algorithm is followed to determine 50% probability of successful defibrillation.

In accordance with the method of this invention, the 50% probability of reaching the upper limit of vulnerability having been determined, and its close correlation with 50% probability of successful defibrillation having been recognized, an appropriate energy level for the pulses of the implantable defibrillator can be readily determined.

In practicing the method of this invention, if the a priori estimate of the 50% probability of reaching the upper limit of vulnerability is above 5.0 Joules, then 5.0 Joules was used as the δ value as set forth above. However, if the a priori estimate of the 50% probability of reaching the upper limit of vulnerability is less than 5.0 Joules, then a δ value of 2.5 Joules has been used. If a 2.5 Joule shock fails to induce ventricular fibrillation, a small shock of 1.0 Joule or less is used to induce ventricular fibrillation. The next shock is again 2.5 Joules.

Summarizing, the algorithm starts to count the four required observations only when the first reversal in response (from no ventricular fibrillation to ventricular fibrillation by decreasing shock strength, or from ventricular fibrillation to no ventricular fibrillation by increasing shock strength) is observed. The shock strength before the reversal of response is the first data point, the shock strength after the reversal of response is second data point. After obtaining the third and the fourth data points by the same up-down algorithm, the fifth data point is predicted based on the results of the fourth data point. The average of these five shock strengths is considered to be the 50% probability of reaching the upper limit of vulnerability.

The foregoing is considered as illustrative only of the principles of the invention, and since numerous modifications and changes will readily occur to those skilled in the art, it is not desired to limit the invention to the exact construction and operation shown and described, and accordingly, all suitable modifications and equivalents may be resorted to, falling within the scope of the present invention.

We claim:

1. A method of determining a defibrillation threshold, said method comprising the steps of;

implanting defibrillation electrodes on or about the heart;

observing the electrical activity of the heart so as to determine the occurrence of ventricular depolarization, such that the periodic occurrence of the mid-upslope of the T-wave (ventricular repolarization) may be determined;

applying an initial electrical test shock to the heart through said defibrillation electrodes with an energy level which is a best a priori estimate of the 50% probability of reaching the upper limit of vulnerability;

sensing for the occurrence of ventricular fibrillation following application of said initial electrical test shock;

applying a subsequent electrical test shock to the heart via said defibrillation electrodes reduced in magnitude by a predetermined amount from initial test shock, if ventricular fibrillation has not occurred as a result of said initial test shock;

again sensing for the occurrence of ventricular fibrillation following application of said subsequent test shock;

repeating the steps of applying subsequent electrical test shocks each reduced in magnitude by said predetermined amount from said prior test shock, and sensing for ventricular fibrillation after each said test shock;

upon sensing ventricular fibrillation following the application of a test shock, the energy level of said test shock which causes ventricular fibrillation being considered a second data point and the energy level of the test shock prior to said test shock which causes ventricular fibrillation being considered a first data point, apply a subsequent test shock increased in magnitude by said predetermined amount from the test shock considered said second data point, said subsequent test shock being considered a third data point;

sense for the occurrence of defibrillation and deliver salvage shock if defibrillation does not occur;

if defibrillation is not sensed following said test shock considered said third data point, apply a test shock increased in magnitude by said predetermined amount from said test shock considered said third data point, said test shock being considered a fourth data point;

again sense for ventricular fibrillation and deliver a salvage shock if defibrillation has not occurred; if ventricular fibrillation is sensed a fifth data point is predicted to be of increased magnitude by said predetermined amount from said shock considered said fourth data point; if ventricular fibrillation is not sensed then a fifth data point in predicted to be of decreased magnitude by said predetermined amount from said shock considered said fourth data point;

if defibrillation has occurred following the application of the test shock considered said third data point, apply a test shock decreased in magnitude by said predetermined amount, said test shock being considered a fourth data point;

again sense for ventricular fibrillation and deliver a salvage shock if ventricular fibrillation occurs; if ventricular fibrillation is sensed said fifth data point is predicted to be of increased magnitude by said predetermined amount from said fourth data point; if ventricular fibrillation is not sensed then said fifth data point is predicted to be of decreased magnitude by said predetermined amount from said fourth data point; and, use the average of said five data points as the shock strength associated with 50% probability of successful defibrillation, for establishing the defibrillation threshold.

* * * * *